(12) United States Patent
Eveland et al.

(10) Patent No.: US 7,002,468 B2
(45) Date of Patent: Feb. 21, 2006

(54) CONTROLLING ACCESS TO A MEDICAL MONITORING SYSTEM

(75) Inventors: Doug C. Eveland, Carlsbad, CA (US); William R. Marable, Carlsbad, CA (US); Bobby E. Rogers, San Diego, CA (US)

(73) Assignee: CardioNet, Inc., San Diego, CA (US)

( * ) Notice: Subject to any disclaimer, the term of this patent is extended or adjusted under 35 U.S.C. 154(b) by 0 days.

(21) Appl. No.: 10/728,631

(22) Filed: Dec. 5, 2003

(65) Prior Publication Data

US 2004/0085186 A1 May 6, 2004

Related U.S. Application Data

(63) Continuation-in-part of application No. 09/841,154, filed on Apr. 23, 2001, now Pat. No. 6,664,893.

(51) Int. Cl.
*G08B 1/08* (2006.01)
(52) U.S. Cl. .................. 340/539.12; 128/903; 340/5.8; 340/573.1; 455/411; 705/2
(58) Field of Classification Search ............. 340/573.1, 340/531, 539.11, 539.12, 5.2, 5.8; 705/2, 705/3, 4; 379/38; 455/404.1, 410, 411; 607/60; 128/903, 904
See application file for complete search history.

(56) References Cited

U.S. PATENT DOCUMENTS

| | | | |
|---|---|---|---|
| 3,478,344 A | 11/1969 | Schwitzgebel et al. | 340/312 |
| 3,768,014 A | 10/1973 | Smith et al. | 324/158 R |
| 3,885,552 A | 5/1975 | Kennedy | 128/2.05 R |
| 3,902,478 A | 9/1975 | Konopasek et al. | 128/2.06 F |
| 3,925,762 A | 12/1975 | Keitlinger et al. | 340/150 |
| 4,173,971 A | 11/1979 | Karz | 128/702 |
| 4,183,354 A | 1/1980 | Sibley et al. | 128/711 |
| 4,211,237 A | 7/1980 | Nagel | 128/698 |
| 4,230,127 A | 10/1980 | Larson | 128/706 |
| 4,241,237 A | 12/1980 | Paraskevakos et al. | 179/2 AM |
| 4,457,315 A | 7/1984 | Bennish | 128/704 |
| 4,531,527 A | 7/1985 | Reinhold, Jr. et al. | 128/696 |
| 4,535,783 A | 8/1985 | Marangoni | 128/711 |
| 4,598,272 A | 7/1986 | Cox | 340/539 |
| 4,651,157 A | 3/1987 | Gray et al. | 342/457 |
| 4,675,656 A | 6/1987 | Narcisse | 340/539 |
| 4,706,689 A | 11/1987 | Man | 128/903 |

(Continued)

FOREIGN PATENT DOCUMENTS

DE 4414 907 6/1995

(Continued)

*Primary Examiner*—Thomas Mullen
(74) *Attorney, Agent, or Firm*—Fish & Richardson P.C.

(57) ABSTRACT

Access to a medical monitoring system, which includes a patient-portable monitoring device and an associated monitoring service at a central unit, is controlled by inputting a set of identification data elements into a medical monitoring device, which then establishes a communication link with a central unit and communicates the set of identification data elements to the central unit. The medical monitoring device and the central unit cooperatively determine whether the medical monitoring device may be activated for rendering medical monitoring device service, by evaluating the set of identification data elements as to whether they meet a set of basic structural requirements, and obtaining financial or other authorization from a third-party source. In the event that the identification data elements meet the set of basic structural requirements and the authorization is obtained, the central unit issues an activation signal to the medical monitoring device over the communication link.

21 Claims, 3 Drawing Sheets

U.S. PATENT DOCUMENTS

| | | | |
|---|---|---|---|
| 4,742,357 A | 5/1988 | Rackley | 342/457 |
| 4,750,197 A | 6/1988 | Denekamp et al. | 379/58 |
| 4,777,478 A | 10/1988 | Hirsch et al. | 340/573 |
| 4,785,291 A | 11/1988 | Hawthorne | 340/573 |
| 4,819,860 A | 4/1989 | Hargrove et al. | 228/668 |
| 4,952,928 A | 8/1990 | Carroll et al. | 340/825.54 |
| 5,003,984 A | 4/1991 | Muraki et al. | 128/710 |
| 5,113,869 A | 5/1992 | Nappholz et al. | 128/696 |
| 5,172,698 A | 12/1992 | Stanko | 128/697 |
| 5,223,844 A | 6/1993 | Mansell et al. | 342/357 |
| 5,301,105 A | 4/1994 | Cummings, Jr. | 364/401 |
| 5,309,920 A | 5/1994 | Gallant et al. | 128/710 |
| 5,311,197 A | 5/1994 | Sorden et al. | 342/457 |
| 5,318,592 A | 6/1994 | Schaldach | 607/5 |
| 5,321,618 A | 6/1994 | Gessman | 364/413.06 |
| 5,334,974 A | 8/1994 | Simms et al. | 340/990 |
| 5,335,664 A | 8/1994 | Nagashima | 128/696 |
| 5,336,245 A | 8/1994 | Adams Theodore P. | 607/32 |
| 5,348,008 A | 9/1994 | Bornn et al. | 128/642 |
| 5,389,934 A | 2/1995 | Kass | 342/357 |
| 5,394,879 A | 3/1995 | Gorman | 128/707 |
| 5,418,537 A | 5/1995 | Bird | 342/356 |
| 5,422,816 A | 6/1995 | Sprague et al. | 364/449 |
| 5,423,869 A | 6/1995 | Poore | 607/18 |
| 5,458,123 A | 10/1995 | Unger | 128/696 |
| 5,461,365 A | 10/1995 | Schlager et al. | 340/573 |
| 5,470,233 A | 11/1995 | Fruchterman et al. | 434/112 |
| 5,479,482 A | 12/1995 | Grimes | 379/59 |
| 5,487,755 A | 1/1996 | Snell et al. | 607/27 |
| 5,497,149 A | 3/1996 | Fast | 340/988 |
| 5,503,158 A | 4/1996 | Coppock et al. | 128/696 |
| 5,504,491 A | 4/1996 | Chapman | 342/357 |
| 5,515,419 A | 5/1996 | Sheffer | 379/58 |
| 5,522,396 A | 6/1996 | Langer et al. | 128/696 |
| 5,544,661 A | 8/1996 | Davis et al. | 128/700 |
| 5,549,113 A | 8/1996 | Halleck et al. | 128/671 |
| 5,564,429 A | 10/1996 | Bornn et al. | 128/696 |
| 5,568,814 A | 10/1996 | Gallant et al. | 128/672 |
| 5,573,506 A | 11/1996 | Vasko | 604/65 |
| 5,576,952 A | 11/1996 | Stutman et al. | 364/413.02 |
| 5,579,775 A | 12/1996 | Dempsey et al. | 128/670 |
| 5,617,871 A | 4/1997 | Burrows | 128/696 |
| 5,620,472 A | 4/1997 | Rahbari | 607/27 |
| 5,626,624 A | 5/1997 | Schaldach et al. | 607/24 |
| 5,626,630 A | 5/1997 | Markowitz et al. | 607/60 |
| 5,629,678 A | 5/1997 | Gargano et al. | 340/573 |
| 5,634,468 A | 6/1997 | Platt et al. | |
| 5,649,303 A | 7/1997 | Hess et al. | 455/63 |
| 5,652,570 A | 7/1997 | Lepkofker | 340/573 |
| 5,678,562 A | 10/1997 | Sellers | 128/710 |
| 5,704,351 A | 1/1998 | Mortara et al. | 128/630 |
| 5,704,364 A | 1/1998 | Saltzstein et al. | 128/696 |
| 5,704,366 A | 1/1998 | Tacklind et al. | 128/716 |
| 5,713,856 A | 2/1998 | Eggers et al. | 604/64 |
| 5,720,770 A | 2/1998 | Nappholz et al. | 607/30 |
| 5,720,771 A | 2/1998 | Snell | 607/60 |
| 5,724,025 A | 3/1998 | Tavori | 340/573 |
| 5,729,197 A | 3/1998 | Cash | 340/539 |
| 5,730,143 A | 3/1998 | Schwarzberg | 128/710 |
| 5,731,757 A | 3/1998 | Layson, Jr. | 340/573 |
| 5,748,103 A | 5/1998 | Flach et al. | 340/870.07 |
| 5,749,367 A | 5/1998 | Gamlyn et al. | 128/696 |
| 5,749,907 A | 5/1998 | Mann | 607/27 |
| 5,752,976 A | 5/1998 | Duffin et al. | 607/32 |
| 5,759,199 A | 6/1998 | Snell et al. | 607/60 |
| 5,882,300 A | 3/1999 | Malinouskas et al. | 600/300 |
| 5,891,169 A | 4/1999 | Boheim et al. | 607/4 |
| 5,913,827 A | 6/1999 | Gorman | 600/509 |
| 5,913,881 A | 6/1999 | Benz et al. | 607/36 |
| 5,931,791 A | 8/1999 | Saltzstein et al. | 600/513 |
| 5,941,829 A | 8/1999 | Saltzstein et al. | 600/509 |
| 5,944,659 A | 8/1999 | Flach et al. | 600/300 |
| 5,950,110 A | 9/1999 | Hendrickson | 455/1 |
| 5,959,529 A | 9/1999 | Kail, IV | 340/539 |
| 5,964,794 A | 10/1999 | Bolz et al. | 607/121 |
| 5,966,692 A | 10/1999 | Langer et al. | 705/3 |
| 5,970,986 A | 10/1999 | Bolz et al. | 128/899 |
| 5,987,352 A | 11/1999 | Klein et al. | 600/509 |
| 5,987,519 A | 11/1999 | Peifer et al. | 709/230 |
| 6,026,008 A | 2/2000 | Feese | 365/63 |
| 6,038,469 A | 3/2000 | Karlsson et al. | 600/512 |
| 6,046,761 A | 4/2000 | Echerer | |
| 6,073,046 A | 6/2000 | Patel et al. | 600/509 |
| 6,083,248 A | 7/2000 | Thompson | 607/30 |
| 6,088,608 A | 7/2000 | Schulman et al. | 600/345 |
| 6,093,146 A | 7/2000 | Filangeri | 600/300 |
| 6,101,478 A | 8/2000 | Brown | 705/2 |
| 6,102,856 A | 8/2000 | Groff et al. | 600/301 |
| 6,154,674 A | 11/2000 | Meier | 607/23 |
| 6,160,478 A | 12/2000 | Jacobsen | 340/539 |
| 6,181,966 B1 | 1/2001 | Nigram | 607/4 |
| 6,192,274 B1 | 2/2001 | Worzewski | 607/14 |
| 6,225,901 B1 | 5/2001 | Kail, IV | 340/539 |
| 6,245,092 B1 | 6/2001 | Schaldach | 607/1 |
| 6,263,243 B1 | 7/2001 | Lang | 607/17 |
| 6,287,252 B1 | 9/2001 | Lugo | |
| 6,466,793 B1 | 10/2002 | Wallstedt et al. | 455/450 |
| 2002/0143576 A1 | 10/2002 | Nolvak et al. | 705/2 |

FOREIGN PATENT DOCUMENTS

| | | |
|---|---|---|
| EP | 0 484 880 | 11/1991 |
| EP | 0535629 | 4/1993 |
| EP | 0 834 846 | 1/1996 |
| EP | 0 811 959 | 6/1997 |
| EP | 0779057 | 6/1997 |
| EP | 1 072 994 | 1/2001 |
| FR | 2 787 905 | 12/1998 |
| WO | 94/13197 | 6/1994 |
| WO | 96 25877 | 8/1996 |
| WO | 97/00708 | 1/1997 |
| WO | 99/22330 | 5/1999 |
| WO | 99 44494 | 9/1999 |
| WO | 00 30529 | 6/2000 |
| WO | 00 62663 | 10/2000 |
| WO | 01/15056 | 3/2001 |

CONTROLLING ACCESS TO A MEDICAL MONITORING SYSTEM

CROSS-REFERENCE TO RELATED APPLICATION

This application is a continuation-in-part of and claims priority under 35 U.S.C. 120 to U.S. application Ser. No. 09/841,154, filed Apr. 23, 2001 which issued on Dec. 16, 2003 as U.S. Pat. No. 6,664,893, the disclosure of which is incorporated by reference.

BACKGROUND

The following description relates to controlling access to a medical monitoring device and/or a service associated with the device, for example, to help ensure that access to the monitoring device and service are authorized prior to commencing usage.

Advances in sensor technology, electronics, and communications have made it possible for physiological characteristics of patients to be monitored even when the patients are ambulatory and not in continuous, direct contact with a hospital monitoring system. For example, U.S. Pat. No. 5,959,529 describes a monitoring system in which the patient carries a remote monitoring unit with associated physiological sensors. The remote monitoring unit conducts a continuous monitoring of one or more physiological characteristics of the patient according to the medical problem of the patient, such as the heartbeat and its waveform.

One potential issue associated with the use of such medical monitoring devices is establishing whether the patient's health-care-benefit payer has authorized the use of the monitoring device and service. In the absence of a proper authorization, the patient may use the medical monitoring device and incur significant charges, for example, in the form of rental value of the medical monitoring device, telephone charges, charges at the central monitoring system, and charges by medical personnel, and the providers of those goods and services may not get paid. Bad debts—an increasing concern in the medical field generally—tend to be an even greater concern in the case of a portable medical monitoring device and its service where the physical control of the device is in the hands of a third party, such as a prescribing doctor, who does not own the medical monitoring device and is not responsible for improper charges.

SUMMARY

The present inventors recognized a need for an approach to controlling access to medical monitoring devices and their associated services to help ensure that only a properly authorized patient can use the service. Controlling access to a medical monitoring system may be accomplished by a system and/or technique that includes one or more of the following features.

To control access to a medical monitoring system, a computer-based method may involve receiving information indicating that a remote monitoring device (e.g., a patient-portable device configured to monitor one or more physiological aspects of a patient) seeks access (e.g., through one or more communications links including either or both of a wired communication link and a wireless communication link) to a monitoring service hosted by a central unit, and determining whether the remote monitoring device is authorized to access the monitoring service. This determination is based at least in part on authorization data received from a third-party source. Based on a result of the determination, an activation signal is selectively issued to the remote monitoring device.

The determination of whether the remote monitoring device is authorized to access the monitoring service may be performed cooperatively between the remote device and the central unit. Further, the determination of whether the remote monitoring device is authorized to access the monitoring service may include one or both of (i) performing a format check on access data entered into the remote monitoring device and (ii) comparing the entered access data against the third-party authorization data.

The access control method may further include maintaining, at the central unit, a local database of third-party authorization data to be used in the determination of whether the remote monitoring device is authorized to access the monitoring service. The local authorization database may be updated, for example, periodically or based on a predetermined event or a combination of both.

Selectively issuing the activation signal to the remote monitoring device based on a result of the determination may include issuing the activation signal if the remote monitoring device is determined to be authorized to access the medical monitoring service and refraining from issuing an activation signal if the remote monitoring device is determined to be unauthorized to access the medical monitoring service.

In another aspect, a medical monitoring system centered at a central node includes one or more communications links configured to facilitate communications with remote monitoring devices (e.g., a patient-portable device configured to monitor one or more physiological aspects of a patient) and one or more third-party authorization sources. The medical monitoring system also includes at least one programmable processor configured to perform various operations. These operations may include hosting a medical monitoring service (e.g., implemented at least in part by one or more software processes), receiving information indicating that a remote monitoring device seeks access to the medical monitoring service hosted by a central unit, determining, based at least in part on authorization data received from a third-party authorization source, whether the remote monitoring device is authorized to access the monitoring service, and based on a result of the determination, selectively issuing an activation signal to the remote monitoring device.

The programmable processor may further be configured to maintain at the central node a local database of third-party authorization data to be used in the determination of whether the remote monitoring device is authorized to access the monitoring service. The local authorization database may be updated based on data received from the one or more third-party authorization sources. Updating may occur periodically or based on a predetermined event or a combination of both.

The programmable processor may further be configured to determine whether the remote monitoring device is authorized to access the monitoring service by one or both of (i) performing a format check on access data entered into the remote monitoring device and (ii) comparing the entered access data against the third-party authorization data.

The programmable processor may be configured to issue the activation signal to the remote monitoring device if the remote monitoring device is determined to be authorized to access the medical monitoring service and to refrain from issuing an activation signal if the remote monitoring device is determined to be unauthorized to access the medical monitoring service.

In another aspect, a portable medical monitoring device includes a transceiver for communicating with a central node, a user interface for communicating with a user of the device, and a programmable processor configured to perform various operations. These operations may include receiving user input specifying user-specific information, transmitting the received user input to the central node for third-party authorization based at least in part on the user-specific information, and selectively providing the user with access to a monitoring service hosted at the central node based on a result of the third-party authorization.

The programmable processor further may be configured to perform a format check on the received user input to determine whether the user input meets one or more predetermined criteria. If the user input is determined not to meet one or more of the predetermined criteria, the programmable processor may refrain from transmitting the received user input to the central station and/or may deny access to the monitoring service. In addition, the programmable processor may be configured to provide access to the monitoring service if the device receives an activation signal from the central node and to deny access to the monitoring service if the device fails to receive an activation signal from the central node.

Among other potential advantages, the systems and techniques described here may facilitate controlling access to medical monitoring devices and associated services. The approach may help to ensure that service is initiated and continued only for persons who are properly authorized to have the service. For example, the present approach may activate the medical monitoring device and its corresponding service only for a person who provides proper identification data and is financially and otherwise properly authorized for the service. As a result, the chances of a wrong person being monitored may tend to be reduced. The activation process, which may involve the input of proper identification data, may be quick and largely transparent to the person seeking the service.

The systems and techniques described here may help to ensure that medical monitoring device services are provided only to properly identified and authorized persons. They may also help to ensure that all persons and agencies responsible for the medical monitoring device and the services are coordinated in their approval of rendering service to the particular patient and in effect have approved the provision of service and the type of service to be provided. Potential legal and financial liability may thereby be reduced. Other features and advantages will be apparent from the following detailed description, the accompanying drawings, and the claims.

DETAILED DESCRIPTION

Figure 1:
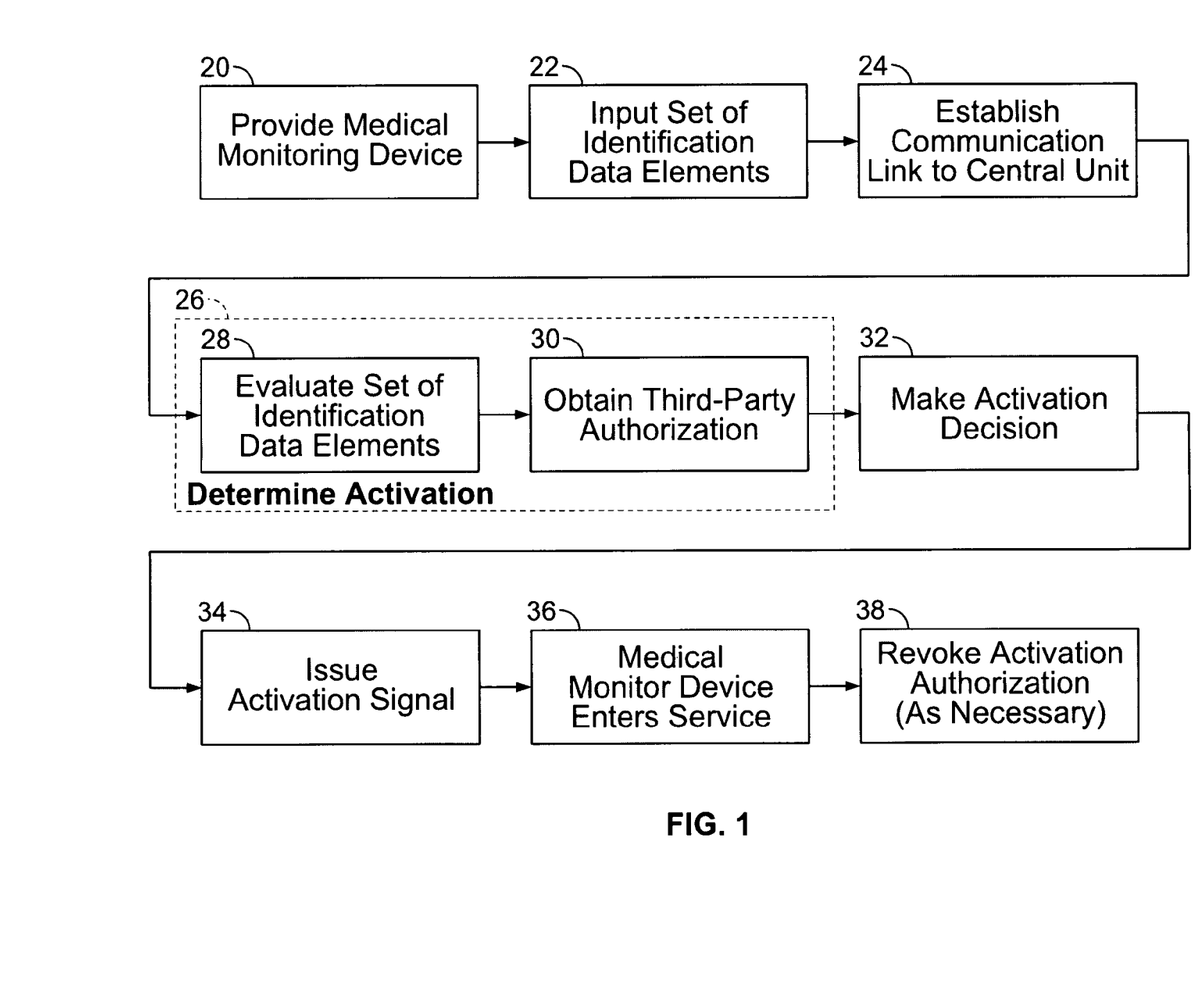
FIG. 1 is a flow diagram of a method of controlling access to a medical monitoring device and/or an associated service.

FIG. 1 depicts a flow diagram of a method of controlling access to a medical monitoring device and/or service. A medical monitoring device and its associated system are provided (20). The medical monitoring device and medical monitoring system may be of any operable type, such as that disclosed in U.S. Pat. No. 5,959,529 (hereafter, "the '529 patent"), whose disclosure is incorporated by reference in its entirety, and/or modified as discussed herein.

Figure 2:
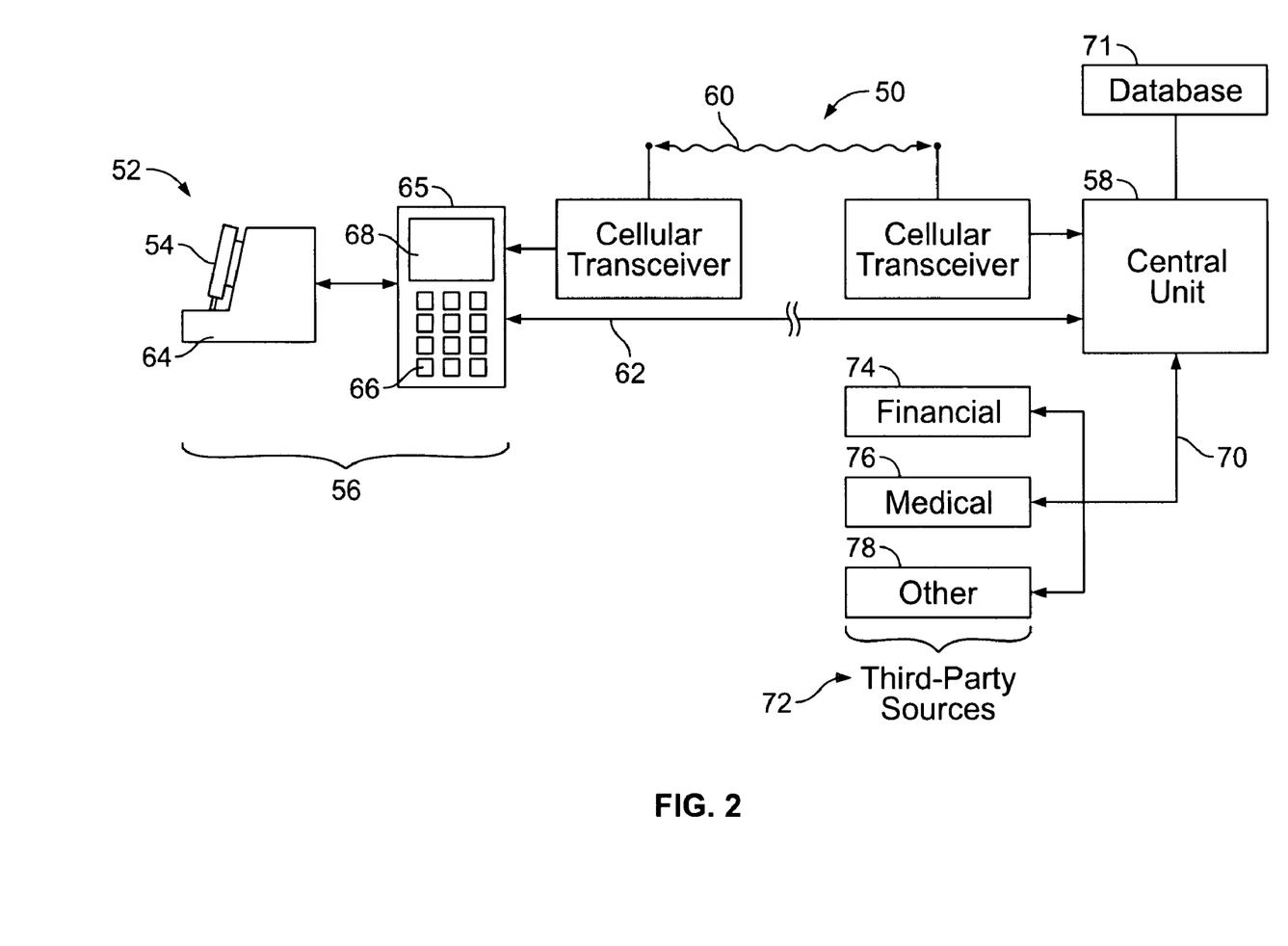
FIG. 2 is a schematic illustration of a system for implementing the method of FIG. 1.

FIG. 2 depicts details, in block diagram form, of a medical monitoring system 50 that includes a medical monitoring device system 52, which in turn comprises a medical monitoring device 54 and a base station 56. The medical monitoring device 54 may be a portable or remote monitoring unit of the type generally described in the '529 patent. The base station 56 has communication access to a central unit 58 through a communication link such as a wireless cellular telephone transceiver link 60 and/or a telephone land-line 62. Alternatively, or in addition, communication links can be established by other available means, among others, such as wired or wireless networks that implement communications protocols and standards such IP (Internet protocol), WiFi (IEEE 802.11x), WiMax (IEEE 802.16x), and GPRS (General Packet Radio Service). The central unit 58, typically maintained at a central node or location, may in practice be composed of multiple computer systems distributed across, or even outside of, the central node.

In the implementation shown in FIG. 2, the base station 56 has a base station cradle 64 that is configured to receive the medical monitoring device 54 therein and establishes communication between the medical monitoring device 54 and an input/output device 65 that typically includes a microprocessor, communications controller, and communications hardware and/or software to establish the links 60 and/or 62. The input/output device 65 has a keypad 66 for inputting information and a display 68 to view the input information and other information to be displayed, as well as information transmitted to the input/output device 65.

The central unit 58 has communications access to a variety of databases 71 and to third-party sources 72, typically by telephone land-line, network or other connection 70. The databases 71 may include prior patient records, general records, and the like. The third-party sources 72 may include, for example, financial sources 74, medical sources 76, and other sources 78. A financial source might be, for example, an insurance company, the social-security administration, or a credit-granting company. A medical source might be, for example, a specialist physician whose authorization is required before commencing the monitoring of the patient. Other third-party sources might be, for example, the company that maintains the medical monitoring device 54 and which is consulted to be certain that the specific medical monitoring device to be activated is approved for service.

The base station 56, when not prescribed or otherwise assigned and distributed to a patient to be monitored, ordinarily is in the custody the office of the agency that is providing the medical monitoring device 54 to a patient for the purpose of monitoring physiological parameters of the patient. Such an agency could be, for example, the patient's physician or a hospital. When the agency undertakes to provide the medical monitoring device 54 to the patient, for example, to take home, the medical monitoring device 54 is docked with the base station 56, and the procedures described in relation to subsequent portions of FIG. 1 are followed.

Returning to FIG. 1, a set of identification data elements (22) are input into the medical monitoring device system 52 through the keypad 66 of the input/output device 65 of the base station 56 in the system 50 of FIG. 2. The identification data elements may include, for example, a patient name, a patient address, a patient social security number, a patient sex, and an identification of the third-party financial source.

The identifier of the medical monitoring device 54, such as its serial number, may be manually input in step 22, but more normally the identifier is automatically made available by the medical monitoring device 54 to the base station 56.

The base station 56 may perform a preliminary evaluation of the set of identification data elements, for example, such as to determine by using a software utility program whether the identification data elements meet a set of one or more format requirements. Such basic format requirements may be specified for each of the identification data elements. For example, a format requirement may specify that a patient name is to include only alphanumeric characters. If as typed into the keyboard the patient name includes other characters (e.g., a percent sign %), software running in the base station can recognize the error and provide an input diagnostic message through the display 68 to prompt the input of correct information. In another example, a format requirement may specify that a user's social security number must contain 9 numerical digits and may not contain letters or other characters.

After what appears from the preliminary format evaluation to be a set of correct identification data elements is input to the medical monitoring device system 52, the medical monitoring device system 52 establishes (24) a communication link to the central unit 58. The communication link is preferably through the land-line 62, but may be though the cellular telephone transmission link 60 or another wireless or wired link if the land-line is not available.

The medical monitoring device system 52 and the central unit 58 cooperatively determine whether the medical monitoring device 54 may be activated for rendering medical monitoring device service (26). The final decision is typically made by the central unit 58, although the medical monitoring device system 52 may aid in data processing or may be called upon for additional input, for example, such as when the patient name is found not to match with the social security number in other records.

The activation determination process 26 may include various sub-processes including evaluating the set of identification data elements as to whether they meet a set of basic structural requirements (28) and obtaining third-party authorization (30) from one or more of the third-party sources 72. The sub-processes of evaluating 28 and obtaining 30 are preferably performed automatically. "Automatically" as used means herein that the steps are performed without human action or intervention, except where a discrepancy occurs. The present system is organized to perform the evaluating and obtaining steps entirely by computer procedures, to minimize costs and take advantage of data collections at a variety of locations. Alternatively, the present approach may be performed in whole or in part using manual (i.e., human-performed) sub-processes 28 and 30. In addition, the sub-process 30 of obtaining third-party authorization can be performed either before or during the activation determination process 26. For example, the sub-process 30 may involve updating a locally stored (e.g., at a central unit hosting the medical monitoring service) copy of a third party's database of authorization information, and then performing the sub-process 30 by accessing the local copy of the database instead of accessing the third party's system, which typically would be maintained at a remote location. Updating of the local third-party authorization database may occur based on one or both of the following criteria: (i) periodically (e.g., once a day) or (ii) based on an occurrence of a predetermined event (e.g., the third-party system determines that a certain amount of new authorization data is available and has not yet been copied to the central unit's local database and/or the central unit determines that its local database does not contain needed information).

The set of basic structural requirements to be imposed may include the format requirements evaluated by the base station 56, or may include different or additional structural requirements. For example, the central unit 58 may check the database 71 to attempt to match the input patient name with a social security number that is already in the database 71 from prior medical contacts. If the patient name and the social security number that were input in subprocess 22 do not match, then further inquiry may be made back to the medical monitoring device system 52. The failure to match the name and the social security number may arise from a simple inputting error, which can be corrected with revised input, or it may arise from a fraudulent attempt to obtain medical monitoring services that is detected by the procedures of sub-process 28.

As noted above, obtaining third-party authorization in sub-process 30 may include contacting appropriate third-party sources 72, e.g., either on a dynamic, as-needed basis, and/or ahead of time by periodically replicating a third party's remote database to create a local copy. The financial source 74 may be contacted to determine whether it authorizes the charges associated with the patient monitoring services. This authorization is particularly important for the business interests of the provider of the services, for example, to avoid unpaid billings. Unpaid billings for medical services represents a major loss for many medical service companies. The medical source 76 may be contacted to determine whether it authorizes the patient monitoring. For example, if the prospective patient is being treated by more than one physician, it may be important to obtain authorization from each physician who is treating the patient before medical monitoring services are commenced. In this case, "authorization" signals formal recognition by the authorizing party that monitoring information will be available. Other sources 78 may also be contacted to determine whether they authorize the patient monitoring. For example, it may be desirable to ensure that the company responsible for maintaining the specific medical monitoring device 54 to be activated authorizes its use. If a prior user had reported a problem and the specific medical monitoring device 54 had been taken out of service for repair, but was mistakenly to be re-activated without being repaired, the company responsible for the maintenance could prevent its activation at this stage.

Thus, the procedures in sub-process 26 act as a "sign off" by a number of checks and third-parties to minimize the possibility that a medical monitoring device will be wrongly issued to a patient and activated. If the sign-offs are not completed, the medical monitoring device is not activated until the reason for the non-completion may be investigated. It is expected that in the great majority of cases, the activation determination process 26 will be completed without incident and so rapidly that the checking will be transparent to the patient and the issuer of the medical monitoring device.

Based on results of the activation determination process, the activation decision is made (32). The final decision is typically made at the central unit 58, although all or part of the final decision could be made at the base station and/or distributed or made by a system at another location. Typically, the decision is made at the central unit 58 because it has the access to the required information during the activation determination process 26, and because the central unit 58 tends to be more immune to tampering than the base station 56.

In the event that the identification data elements meet the set of basic structural requirements and third-party authorization is obtained, the central unit 58 issues an activation signal (34) to the medical monitoring device system 52 over the communication link 60 or 62. The medical monitoring device 54 is activated and enters service (36).

The "activation signal" may be of any operable type. It may be a software "on" switch that enables the processing of data within a microprocessor in the medical monitoring device 54 or a hardware "on" switch that turns on particular hardware functions such as the communications links built into the medical monitoring device 54. The activation signal may be complex, and may include identification of the patient and the specific medical monitoring device 54 that is associated with that patient. This activation signal may then be transmitted with each subsequent communication between the medical monitoring device 54 and the central unit 58 for identification purposes. In the event that the proper activation signal is not transmitted with each communication, it may be ignored. The activation may be revoked (38) at a later time if the authorization is withdrawn or for other reasons. Upon revocation 38, the signals transmitted by the medical monitoring device 54 are not acted upon, and the patient and/or the issuing authority are notified and requested to return the medical monitoring device 54. As an alternative to revocation 38, the activation signal of step 34 may include a maximum time limit for which activation is authorized, so that a further authorization is required to extend the period of authorized use.

Figure 3:
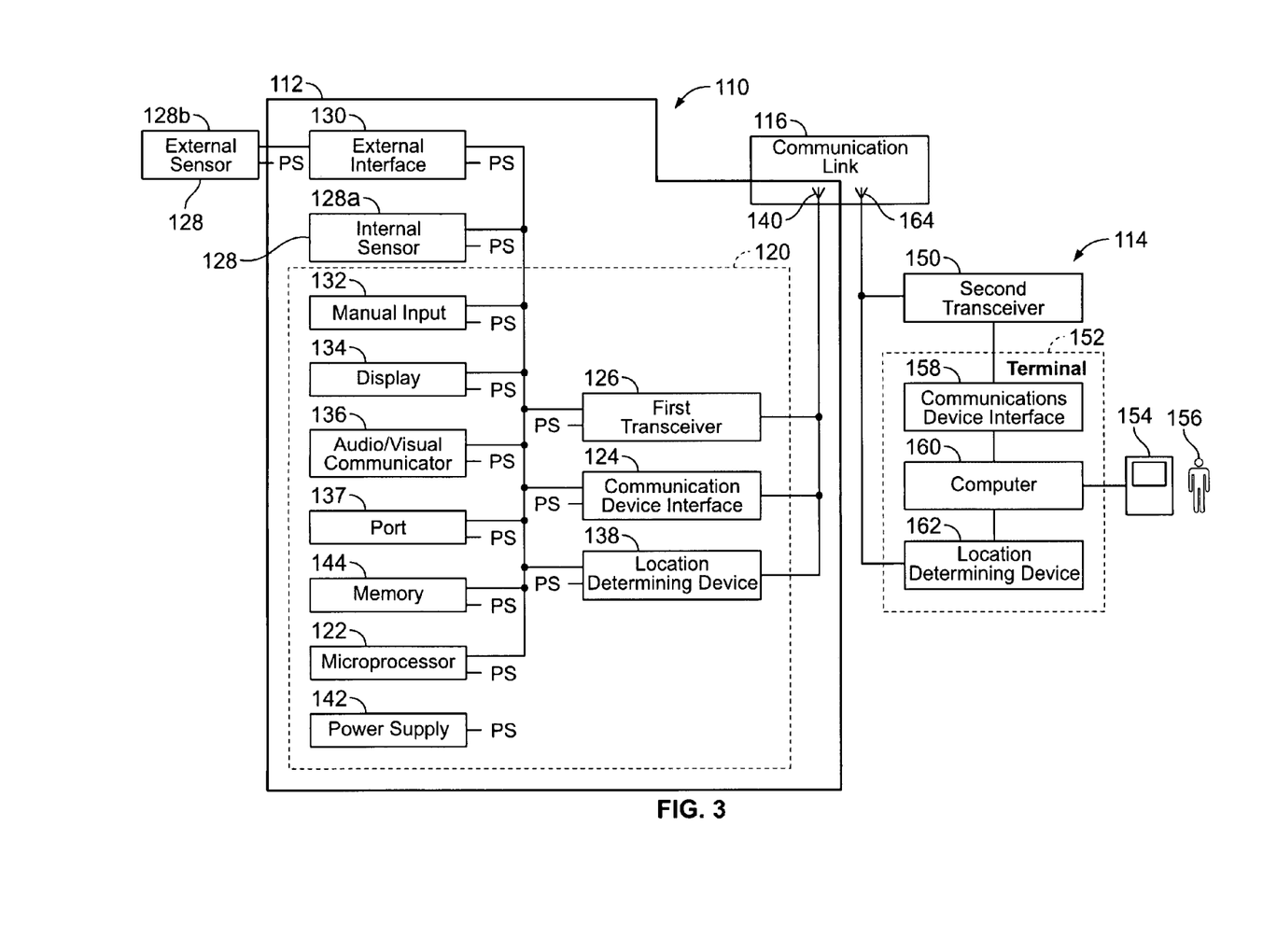
FIG. 3 is a block diagram of an apparatus for remotely monitoring a subject.

As shown in FIG. 3, an apparatus 110 for remotely monitoring and assessing the status of a subject includes a portable monitoring unit 112 and a central monitoring device 114, which may communicate via by a wireless communication link 116.

The portable monitoring unit 112 includes a sensor interface unit 120 having a microprocessor 122 with multiple inputs and outputs, illustrated in a bus architecture. Communication of the microprocessor 122 with the wireless communication link 116, and thence with the central monitoring device 114, is effected through a communications device interface 124 and a first transceiver 126 of the wireless communication link 116. Information is gathered by one or more sensors 128. It is preferred that the wireless communication link 116 be a digital wireless communication link, but an analog link may be used instead. The sensors 128 may include internal sensors 128a embedded in the portable monitoring unit 112 and/or external sensors 128b that are connected to the portable monitoring unit through appropriate external interfaces 130. (In FIG. 3, the external interface 130 is illustrated as part of the portable monitoring unit 112, but it may be external to the portable monitoring unit.) The external sensors 128b may be any type that may be interfaced with the microprocessor 122 through the interface 130. For example, the interface 130 may be a standard serial or parallel interface, a PCMCIA interface, or an Ethernet interface. An external programming device or other device may also be connected to microprocessor 122 through the appropriate external interface 130.

An optional manual input device 132 communicating with the microprocessor 122 is accessible from the exterior of the portable monitoring unit 112, to allow a user or subject of the portable monitoring unit to provide information to the microprocessor 122. The manual input device 132 may be as simple as a switch such as a push button, or more complex such as a keypad. Optionally, a display 134, such as a liquid crystal display, and an audio and/or visual communicator 136, such as a tone generator, speaker, or flashing light, may be provided to signal the user of the portable monitoring unit 112 to take responsive action. An external port 137, such as a serial or a parallel communication port, is provided to permit information or reprogramming instructions to be input to the microprocessor 122 at the site of the portable monitoring unit 112. (A compatible sensor may also be connected through the external port 137.) The manual input device 132, the display 134, the audio and or visual communicator 136, and external port 137 are each optional features that may be provided for specific applications.

The microprocessor 122 may be a Multi-Chip Package (MCP) such as the currently available Vadem VG330, the Advanced Micro Devices AMD Elan SC400, the NEC HHT-ASSP, or the ZF MicroSystems SMX/386. The microprocessor includes a power management unit which permits the microprocessor to be placed into an inactive state or awakened to an active state by a proper signal. The power management achieves conservation of the power of the power supply 142. The microprocessor is typically provided with memory 144, which may be a random access memory, a readonly memory, a mass storage device, or any combination of these types of memory. This memory may be shared with other components of the portable monitoring unit 112. The first transceiver 126 may be a single-board digital wireless module such as a WIT915 or WIT2500M marketed by Digital Wireless Corporation, with the appropriate interface 124. The first transceiver 126 has its own power management unit that permits the transceiver to be placed into an inactive state or awakened to an active state by a proper signal.

A location-determining device 138 is provided so that the location of the portable monitoring unit 112 may be determined. The location-determining device 138 is preferably a global positioning system (GPS) receiver having an antenna 140 shared with the antenna of the first transceiver 126. The GPS receiver may be a MicroTracker LP global positioning system receiver module available from Rockwell Semiconductor Systems. Other types of location-determining devices 138 such as those based upon cellular cell-site position triangulations, LORAN, and the like, may also be used.

A power supply 142 such as a battery provides power for the components of the portable monitoring unit 112 requiring power, and optionally for the external sensor 128b and the external interface 130. In FIG. 3, the power connections between the powered components and the power supply 142 are indicated by "PS" to avoid the need for drawing the interconnections that would obscure the data-communications paths.

The central monitoring device 114 includes at least a second transceiver 150 of the wireless communication link 116, to establish communications between the first transceiver 126 of the portable monitoring unit 112 and the central monitoring device 114. Typically, the central monitoring device 114 further includes a terminal 152 having a communications device interface 158 to the second transceiver 150, and connections to a display 154 that may be viewed by an operator 156. The terminal 152 may be a simple manual system, or, preferably, it may be a more complex as illustrated. In this more complex terminal 152, there is a computer 160 that communicates with the display 154 and communicates with and oversees the operations of the portable monitoring unit 112 in the manner to be discussed subsequently. The central monitoring device 114 may also be provided with a location-determining device 162, particularly if the central monitoring is movable or portable and its location must be determined. The location-determining device 162 has an antenna 164 shared with the antenna of the second transceiver 150. The location-determining devices 138 and 162 are typically selected to be compatible. If, for example, the location-determining device 138 is an autonomous GPS receiver, the location-determining device 162 normally is also a GPS receiver. On the other hand, the location-determining technique may utilize a triangulation, time-of-flight, or other type of measurement that requires. coordination between the location-determining devices 138 and 162, which are then chosen with that technique in mind.

Other embodiments are within the scope of the following claims.

What is claimed is:

1. A computer-based method for controlling access to a medical monitoring system, the method comprising:
   receiving information indicating that a remote monitoring device seeks access to a monitoring service hosted by a central unit, the remote monitoring device comprising a patient-portable device configured to monitor one or more physiological aspects of a patient;
   determining whether the remote monitoring device is authorized to access the monitoring service, the determination being based at least in part on authorization data received from a third-party source; and
   based on a result of the determination, selectively issuing an activation signal to the remote monitoring device.

2. The method of claim 1 wherein the determination of whether the remote monitoring device is authorized to access the monitoring service is performed cooperatively between the remote device and the central unit.

3. The method of claim 1 wherein the determination of whether the remote monitoring device is authorized to access the monitoring service comprises one or both of (i) performing a format check on access data entered into the remote monitoring device and (ii) comparing the entered access data against the third-party authorization data.

4. The method of claim 1 further comprising maintaining at the central unit a local database of third-party authorization data to be used in the determination of whether the remote monitoring device is authorized to access the monitoring service.

5. The method of claim 4 further comprising updating the local third-party authorization database.

6. The method of claim 5 wherein updating of the local third-party authorization database occurs periodically or based on a predetermined event or a combination of both.

7. The method of claim 1 wherein selectively issuing the activation signal to the remote monitoring device based on a result of the determination comprises issuing the activation signal if the remote monitoring device is determined to be authorized to access the medical monitoring service and refraining from issuing an activation signal if the remote monitoring device is determined to be unauthorized to access the medical monitoring service.

8. The method of claim 1 wherein the remote monitoring device communicates with the central unit through one or more communications links including either or both of a wired communication link and a wireless communication link.

9. A medical monitoring system centered at a central node, the medical monitoring system comprising:
   one or more communications links configured to facilitate communications with a plurality of patient-portable remote monitoring devices and one or more third-party authorization sources, the remote monitoring devices being configured to monitor one or more physiological aspects of a patient;
   at least one programmable processor configured to perform operations comprising:
      host a medical monitoring service, the medical monitoring service being implemented at least in part by one or more software processes;
      receive information indicating that a remote monitoring device seeks access to the medical monitoring service;
      determine, based at least in part on authorization data received from a third-party authorization source, whether the remote monitoring device is authorized to access the monitoring service; and
      based on a result of the determination, selectively issue an activation signal to the remote monitoring device.

10. The system of claim 9 wherein the programmable processor is further configured to maintain at the central node a local database of third-party authorization data to be used in the determination of whether the remote monitoring device is authorized to access the monitoring service.

11. The system of claim 9 further comprising a local database of third-party authorization data and wherein the programmable processor further is configured to update the local authorization database based on data received from the one or more third-party authorization sources.

12. The system of claim 11 wherein the programmable processor is further configured to determine whether the remote monitoring device is authorized to access the monitoring service by one or both of (i) performing a format check on access data entered into the remote monitoring device and (ii) comparing the entered access data against the third-party authorization data.

13. The system of claim 11 wherein the programmable processor updates the local authorization database periodically or based on a predetermined event or a combination of both.

14. The system of claim 9 wherein the programmable processor issues the activation signal to the remote monitoring device if the remote monitoring device is determined to be authorized to access the medical monitoring service and refrains from issuing an activation signal if the remote monitoring device is determined to be unauthorized to access the medical monitoring service.

15. A portable medical monitoring device configured to monitor one or more physiological aspects of a patient, the device comprising:
   a transceiver for communicating with a central unit;
   a user interface for communicating with a user of the device; and
   a programmable processor configured to perform operations comprising:
      receive user input specifying user-specific information;
      transmit the received user input to the central unit for third-party authorization based at least in part on the user-specific information; and
      selectively provide the user with access to a monitoring service hosted at the central unit based on a result of the third-party authorization.

16. The device of claim 15 wherein the programmable processor further is configured to perform a format check on the received user input to determine whether the user input meets one or more predetermined criteria.

17. The device of claim 16 wherein the programmable processor is further configured to refrain from transmitting the received user input to the central station if the user input is determined not to meet one or more of the predetermined criteria.

18. The device of claim 17 wherein the programmable processor is further configured to deny access to the monitoring service if the user input is determined not to meet one or more of the predetermined criteria.

19. The device of claim 15 wherein the programmable processor provides access to the monitoring service if the device receives an activation signal from the central unit and denies access to the monitoring service if the device fails to receive an activation signal from the central unit.

20. A computer-based method for controlling access to a medical monitoring system, the method comprising:

receiving information indicating that a patient-portable remote monitoring device seeks access to a monitoring service hosted by a central unit, the patient-portable remote monitoring device configured to monitor one or more physiological aspects of a patient;

determining whether the patient-portable remote monitoring device is authorized to access the monitoring service, the determination being based at least in part on authorization data received from a third-party source; and based on a result of the determination, selectively issuing an activation signal to the patient-portable remote monitoring device.

21. A medical monitoring system centered at a central node, the medical monitoring system comprising:

one or more communications links configured to facilitate communications with a plurality of patient-portable remote monitoring devices and one or more third-party authorization sources, the patient-portable remote monitoring devices being configured to monitor one or more physiological aspects of a patient;

at least one programmable processor configured to perform operations comprising:

host a medical monitoring service, the medical monitoring service being implemented at least in part by one or more software processes;

receive information indicating that a first patient-portable remote monitoring device seeks access to the medical monitoring service;

determine, based at least in part on authorization data received from a third-party authorization source, whether the first patient-portable remote monitoring device is authorized to access the monitoring service; and based on a result of the determination, selectively issue an activation signal to the first patient-portable remote monitoring device.

* * * * *